US00PP35264P3

(12) United States Plant Patent
Holtmaat

(10) Patent No.: US PP35,264 P3
(45) Date of Patent: Jul. 11, 2023

(54) ***HEUCHERA* PLANT NAMED 'TONCKA 390'**

(50) Latin Name: ***Heuchera* hybrid**
Varietal Denomination: Toncka 390

(71) Applicant: Henricus Maria Joseph Holtmaat, Zuidwolde (NL)

(72) Inventor: Henricus Maria Joseph Holtmaat, Zuidwolde (NL)

(73) Assignee: AB KWEKERSRECHTEN B.V., Zuidwolde (NL)

( * ) Notice: Subject to any disclaimer, the term of this patent is extended or adjusted under 35 U.S.C. 154(b) by 0 days.

(21) Appl. No.: 17/961,745

(22) Filed: Oct. 7, 2022

(65) Prior Publication Data

US 2023/0157193 P1 May 18, 2023

(30) Foreign Application Priority Data

Nov. 16, 2021 (QZ) ..... PBR 20212950

(51) Int. Cl.
*A01H 5/02* (2018.01)
*A01H 6/80* (2018.01)

(52) U.S. Cl.
USPC ..... Plt./440
CPC ..... *A01H 6/80* (2018.05)

(58) Field of Classification Search
USPC ..... Plt./440
CPC ... A01H 5/02; A01H 5/12; A01H 5/00; A01H 6/80
See application file for complete search history.

(56) References Cited

U.S. PATENT DOCUMENTS

PP29,207 P2 * 4/2018 Hansen ..... A01H 5/02 Plt./440

* cited by examiner

*Primary Examiner* — June Hwu
(74) *Attorney, Agent, or Firm* — Penny J Aguirre

(57) ABSTRACT

A new cultivar of *Heuchera* plant named 'Toncka 390' that is characterized by its strong and sturdy plant habit, its leaf colors that are grey and tinged grey-purple, its floriferous blooming habit, and its flowers that are white and moderately red-purple in color.

2 Drawing Sheets

Botanical classification: *Heuchera* hybrid.
Cultivar designation: 'Toncka 390'.

CROSS REFERENCE TO A RELATED APPLICATION

This application claims priority to European Community Plant Variety Office (CPVO) Plant Breeder's Rights Application No. No. 2021/2950, filed Nov. 16, 2021. The Applicant received the information for the Plant breeders' rights application directly from the Inventor.

BACKGROUND OF THE INVENTION

The present invention relates to a new and distinct cultivar of *Heuchera* of hybrid origin, botanically known as *Heuchera* 'Toncka 390' and is hereinafter referred to by its cultivar name 'Toncka 390'.

The new cultivar was discovered as a chance seedling in a trial field by the Inventor in Zuidwolde, The Netherlands in July of 2019. The source of the seedling was from seed collected in 2019 from open pollinated plants in a trial field that contained numerous unnamed and unpatented proprietary *Heuchera* seedlings from the Inventor's breeding program. The parentage of 'Toncka 390' is therefore unknown.

Asexual propagation of the new cultivar was first accomplished under the direction of the Inventor by tissue culture initiated from meristem tissue in February of 2020 in Heerhugowaard, The Netherlands. Asexual propagation of the new cultivar by tissue culture has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Toncka 390' as a new and unique cultivar of *Heuchera*.

1. 'Toncka 390' exhibits a strong and sturdy plant habit.
2. 'Toncka 390' exhibits leaf colors that are grey and tinged grey-purple.
3. 'Toncka 390' exhibits a floriferous blooming habit.
4. 'Toncka 390' exhibits flowers that are white and moderately red-purple in color.

'Toncka 390' can be most closely compared to the *Heuchera* cultivars 'Silver Gumdrop' (U.S. Plant Pat. No. 29,207) and 'TNHEUFP' (U.S. Plant Pat. No. 26,358). 'Silver Gumdrop' differs from 'Toncka 390' in having foliage that is more grey in color and tinged with more purple and flowers that are red in color. 'TNHEUFP' is similar to 'Toncka 390' in foliage coloration. 'TNHEUFP' differs from 'Toncka 390' in having leaves that are smaller in size and in being much less floriferous.

BRIEF DESCRIPTION OF THE DRAWINGS

The accompanying color photographs illustrate the overall appearance and distinct characteristics of the new *Heu-*

*chera*. The photographs were taken of a plant 18 months in age of the new cultivar as grown outdoors in a 19-cm containers in Zuidwolde, The Netherlands.

Figure 1:
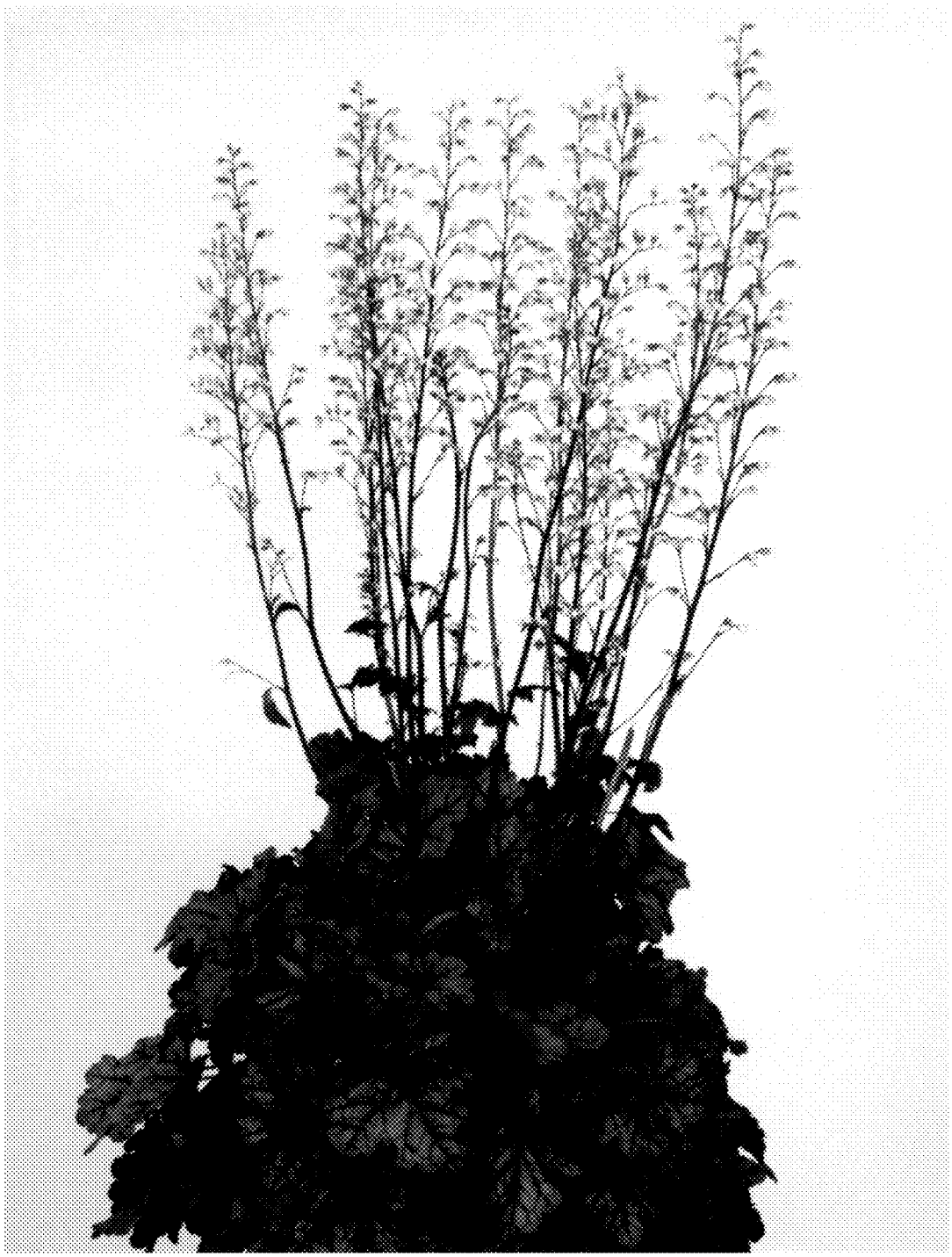

The photograph in FIG. 1 provides a side view of the plant of 'Toncka 390' in bloom.

Figure 2:
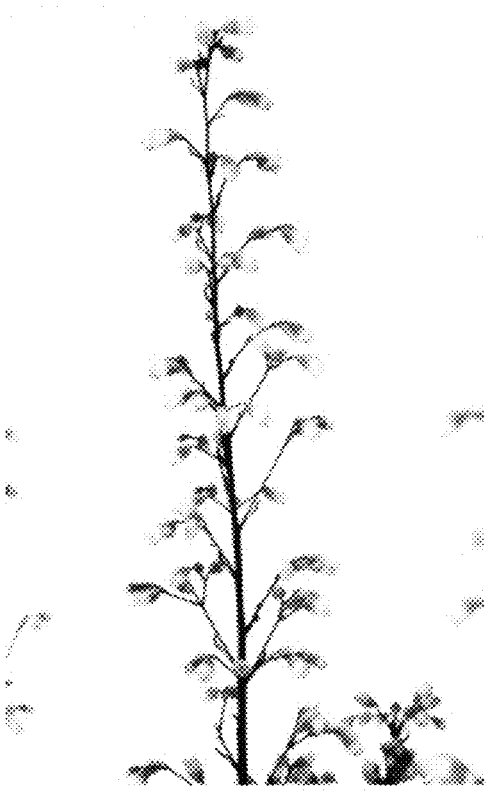

The photograph in FIG. 2 provides a close up of an inflorescence of 'Toncka 390'.

Figure 3:
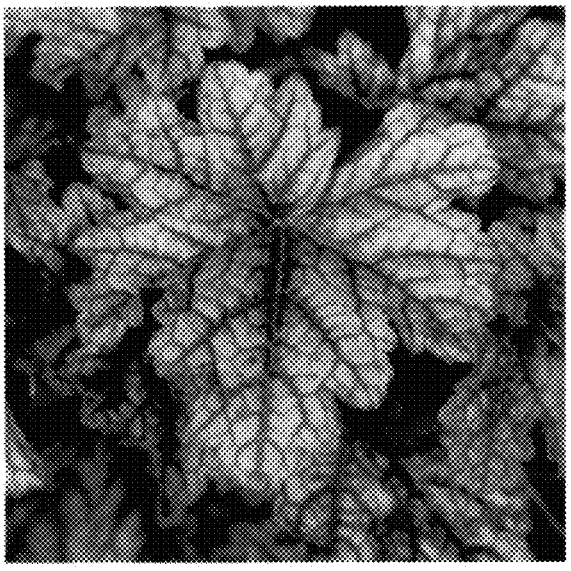

The photograph in FIG. 3 provides a close up view of the foliage of 'Toncka 390'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 18 month-old plants of the new cultivar as grown outdoors in 19-cm containers in Zuidwolde, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—10 weeks, midsummer to late summer in The Netherlands.

*Plant type*.—Herbaceous perennial.

*Plant habit*.—Globular with inflorescences held above the foliage.

*Height and spread*.—An average of 30 cm in height (soil level to top of foliar plane), average of 90 cm in height (soil level to top of floral plane) and 55 cm in spread as an 18 month-old plant.

*Cold hardiness*.—At least in U.S.D.A. Zone 3.

*Diseases and pests*.—No susceptibility or resistance to pests or diseases has been observed.

*Root description*.—Fibrous roots on woody rootstalks, 158D in color.

*Propagation*.—Tissue culture.

*Root development*.—An average of 3 weeks for root initiation, 6 weeks to produce a rooted cutting.

*Growth rate*.—Vigorous.

*Branching habit*.—Flowering stems emerge from basal rosette, an average of 1 rosette per plant, no lateral branches.

Foliage description:

*Leaf shape*.—Orbicular, slightly concave.

*Leaf division*.—Simple.

*Leaf base*.—Hastate, lobes slightly to moderately overlapping.

*Leaf apex*.—Short and abruptly acute.

*Leaf venation*.—Laciniate, upper surface 162D, lower surface 187A.

*Leaf margins*.—Crenate with abruptly acute tips on each tooth, moderately undulate.

*Leaf attachment*.—Petiolate.

*Leaf arrangement*.—Alternate in basal rosettes.

*Leaf lobes*.—Lobed, an average of 7 to 9 lobes, medium in depth, divergent, lobe margins free to touching.

*Leaf surface*.—Upper surface; smooth, pubescent, moderately velvety, matte, non-rugose, lower surface; smooth, pubescent, matte, non-rugose, both surfaces moderately covered with very short strigose hairs, 0.3 mm in length, closest to NN155D in color; hard to measure color based on sparseness and the small size.

*Leaf color*.—Young upper surface; 200B to 200C, young lower surface; N79A and N186D, mature upper surface; 201A to 201B, tinged N187C, fading later in the season to 198A to 198B, mature lower surface; 187A.

*Leaf size*.—An average of 13.5 cm in length and 13.4 cm in width.

*Leaf quantity*.—An average of 8 per basal rosette.

*Petioles*.—An average of 16.8 cm in length and 3 mm in diameter, medium strength, both surfaces moderately glossy, color; upper and lower surface 187A, moderately covered with short soft hairs, average of 0.5 mm in length, hairs on both sides closest to NN155D in color; hard to measure color based on sparseness and the small size.

*Stipules*.—Leafy stipule at the base of each leaf, average 1 cm in length, average 5 mm in width, acute tip, 71A in color.

Flower description:

*Inflorescence type*.—Numerous small bell-shaped flowers arranged on panicles on peduncles emerging from a basal rosette.

*Inflorescence size*.—An average of 41.5 cm in height and 8.6 cm in diameter.

*Inflorescence number*.—An average of 20.

*Flower fragrance*.—None.

*Flower quantity*.—Average of 120 flowers per flowering stem, 2,000 per plant.

*Flower lastingness*.—Average of one week.

*Flower buds*.—Obovate in shape, an average of 5 mm in length and 3 mm in diameter, color; 155A, tinged at the top and lower half with 187D, surface is matte and densely covered with very short glandular hairs; an average of 0.3 mm in length and too small to measure color.

*Flower aspect*.—Nodding to slightly outward.

*Flower type*.—Single, campanulate.

*Flower size*.—Average of 6 mm in height and diameter.

*Petals*.—Average of 5, rotate arrangement and implanted in the hypanthium at base, oblanceolate in shape, margin is entire, apex is acute, base is long acuminate, upper and lower surface are glabrous, smooth and matte, an average of 3 mm in length and 1 mm in width, color when opening and fully open upper and lower surface; NN155D.

*Calyx*.—Campanulate, sepals fused to hypanthium, 8 mm in length, 6 mm in diameter.

*Sepals*.—An average of 5, lower 50% fused into campanulate hypanthium, short oblong in shape, an average of 8 mm in length and 3 mm in width, margin is entire and fused into hypanthium, apex is obtuse, color; when opening and fully open upper surface NN155D, tip and lower half 187D, when opening and fully open lower surface NN155D, tip and lower half 71D, both surfaces are matte and densely covered with very short glandular hairs an average of 0.2 mm in length and to small to measure color.

*Peduncle*.—An average of 73.2 cm in length and 4 mm in diameter, color; a blend of N186C and 187A, primary flower aspect 75°, secondary peduncle aspect to main peduncle 32.5°, moderate in strength, surface moderately glossy and densely covered with very short soft glandular hairs; average of 0.2 mm in length, NN155D in color.

*Pedicels*.—An average of 2 mm in length and 0.5 mm in diameter, N170A in color, primary flower aspect straight on top of secondary pedicel, secondary and tertiary flower aspect is 45°, moderate in strength, surface matte and moderately covered with very short soft glandular hairs; average of 0.2 mm in length and too small to measure color.

Reproductive organs:

*Gynoecium*.—Pistils; 2, 4.5 mm in length, stigma; club-shaped, 0.2 mm in diameter, style; an average of 4.25 mm in length and NN155D in color, ovary; 146D in color.

*Androecium*.—Stamens; 5, anthers; ovate in shape, average of 0.4 mm in length and width, 171C in color, filament; 3.5 mm in length and NN155D in color, pollen; low in quantity, 28A in color.

*Seed/fruit*.—No fruit or seeds have been observed to date.

It is claimed:

1. A new and distinct cultivar of *Heuchera* plant named 'Toncka 390' as herein illustrated and described.

* * * * *